United States Patent [19]

Rodriguez

[11] Patent Number: 5,927,276

[45] Date of Patent: Jul. 27, 1999

[54] DEVICES AND METHODS FOR POSITIONING AND SECURING MEDICAL TUBES

[76] Inventor: Paul Isaac Rodriguez, 4135 Hawkins St., Fremont, Calif. 94538

[21] Appl. No.: 08/890,062

[22] Filed: Jul. 9, 1997

[51] Int. Cl.[6] .............................. A61M 16/00; A62B 9/06
[52] U.S. Cl. ............................. 128/207.17; 128/DIG. 26
[58] Field of Search ..................... 128/200.26, 207.14, 128/207.15, 207.17, 911, 912, DIG. 26, 207.11, 206.19

[56] References Cited

U.S. PATENT DOCUMENTS

| 2,756,742 | 7/1956 | Barton | 128/207.17 |
|---|---|---|---|
| 3,013,556 | 12/1961 | Galleher | 128/207.11 |
| 4,009,509 | 3/1977 | McCormick | 24/16 PB |
| 4,191,180 | 3/1980 | Colley et al. | 128/207.17 |
| 4,744,358 | 5/1988 | McGinnis | 128/207.17 |
| 4,827,923 | 5/1989 | Bishop et al. | 128/207.11 |
| 4,867,154 | 9/1989 | Potter et al. | 128/207.17 |
| 5,046,200 | 9/1991 | Feder | 128/207.11 |
| 5,069,206 | 12/1991 | Crosbie | 128/207.17 |
| 5,174,284 | 12/1992 | Jackson | 128/200.26 |
| 5,295,480 | 3/1994 | Zemo | 128/207.17 |
| 5,383,451 | 1/1995 | DeIulio | 128/207.17 |
| 5,402,776 | 4/1995 | Islava | 128/207.17 |
| 5,413,095 | 5/1995 | Weaver | 128/912 |
| 5,724,677 | 3/1998 | Bryant et al. | 128/207.11 |

*Primary Examiner*—John G. Weiss
*Assistant Examiner*—Joseph F. Weiss, Jr.
*Attorney, Agent, or Firm*—Law Office of Albert J. Dalhuisen

[57] ABSTRACT

The present invention provides devices and methods for positioning and securing medical tubes in a patient's mouth or nose. These devices have frame portions which include an inverted U-shaped portion having an upper jaw portion, two cheek portions and a lower jaw portion. Fasteners are provided to fasten the devices of the current invention on a patient's head. Medical tubes can be inserted in these devices and intubated in a patient's mouth or nose. The medical tubes can be affixed to the frame portions of the devices of the present invention.

35 Claims, 9 Drawing Sheets

DEVICES AND METHODS FOR POSITIONING AND SECURING MEDICAL TUBES

FIELD OF THE INVENTION

The present invention relates to devices and methods for positioning and securing medical tubes. More particularly, the invention relates to devices and methods for positioning and securing medical tubes which are inserted in a patient's mouth or nose. Still more particularly, the invention relates to devices and methods for positioning and securing one or more endotracheal or gastrointestinal tubes to a patient.

BACKGROUND OF THE INVENTION

Endotracheal tubes are inserted into a patient's trachea, to provide a clear passage for air flow to the lungs if the trachea has been damaged. These tubes are also inserted prior to administering a general anesthetic. Endotracheal tubes can be intubated through the mouth or the nose. Feeding tubes are inserted in some patients either in the mouth or in the nose. Additionally, tubes may be used to drain saliva or mucus, or to assist in cleaning a patient's mouth. These various tubes need to be secured in a fixed position relative to the patient. Some patients require tube intubation during a relatively short time period, e.g. during surgery, while others require long term intubation. It is important that each tube is firmly secured in place, in order to prevent accidental removal or re-positioning of the tube.

Various devices and methods have been developed for securing one or more tubes in a patient's mouth or nose. Some of the devices, such as U.S. Pat. No. 5,402,776 (Islava, 1995), cover a substantial part of a patient's mouth making it difficult to access the mouth or to visually inspect the mouth. Other devices, such as U.S. Pat. No. 5,295,480 (Zemo, 1994) cover part of the patient's skin, potentially leading to skin irritation or infection due to saliva, mucus or vomitus seeping in between the skin and the cover.

Devices which cover a substantial portion of the lips, such as the '776 patent, similarly lead to potential lip irritation and infection. Other tube holding devices require a bite block, see for example U.S. Pat. No. 5,069,206 (Crosbie, 1991). Such bite blocks have the known disadvantage of limited access to the mouth or limited visual examination of the patient's mouth.

Frame or wire based medical tube holding devices are disclosed in U.S. Pat. No. 5,383,451 (Delulio, 1995) and U.S. Pat. No. 4,867,154 (Potter et al., 1989). These wire based devices are attached to the patient's head by means of adhesive tape or adhesive patches. Use of adhesive tape or patches, such as disclosed in the '451 and '154 patents makes it difficult to adjust the devices for optimum positioning and can lead to skin irritation. Also, removal of the adhesive tape or patch in order to remove or re-position the device causes discomfort to the patient.

Many of the devices are not readily adaptable to the simultaneous use of several tubes or the simultaneous use of a tube inserted in the mouth and a tube inserted in the nose.

Accordingly, the need exists for improved devices and methods for positioning and securing medical tubes, allowing improved access and visual examination of the mouth while maintaining secure positioning of the tubes and having minimal contact with a patient's mouth, lips or skin.

SUMMARY OF THE INVENTION

The present invention provides novel devices and methods for positioning and securing medical tubes which are intubated in a patient's mouth or nose.

In one embodiment the current invention provides medical tube positioning and securing devices having frame portions which include an inverted U-shaped portion having an upper jaw portion, two cheek portions and a lower jaw portion.

In another embodiment the present invention provides medical tube positioning and securing devices having frame portions which include an inverted U-shaped portion having an upper jaw portion, two cheek portions and a lower jaw portion, wherein the devices are fastened to a patient's head by means of fasteners.

In still another embodiment the current invention provides medical tube positioning and securing devices having frame portions which include an inverted U-shaped portion having an upper jaw portion, two cheek portions, a lower jaw portion and a nose portion.

DETAILED DESCRIPTION OF THE INVENTION

While describing the invention and its embodiments, certain terminology will be utilized for the sake of clarity. It is intended that such terminology include not only the recited embodiments but all equivalents which perform substantially the same function, in substantially the same manner to achieve substantially the same result.

Figure 1:
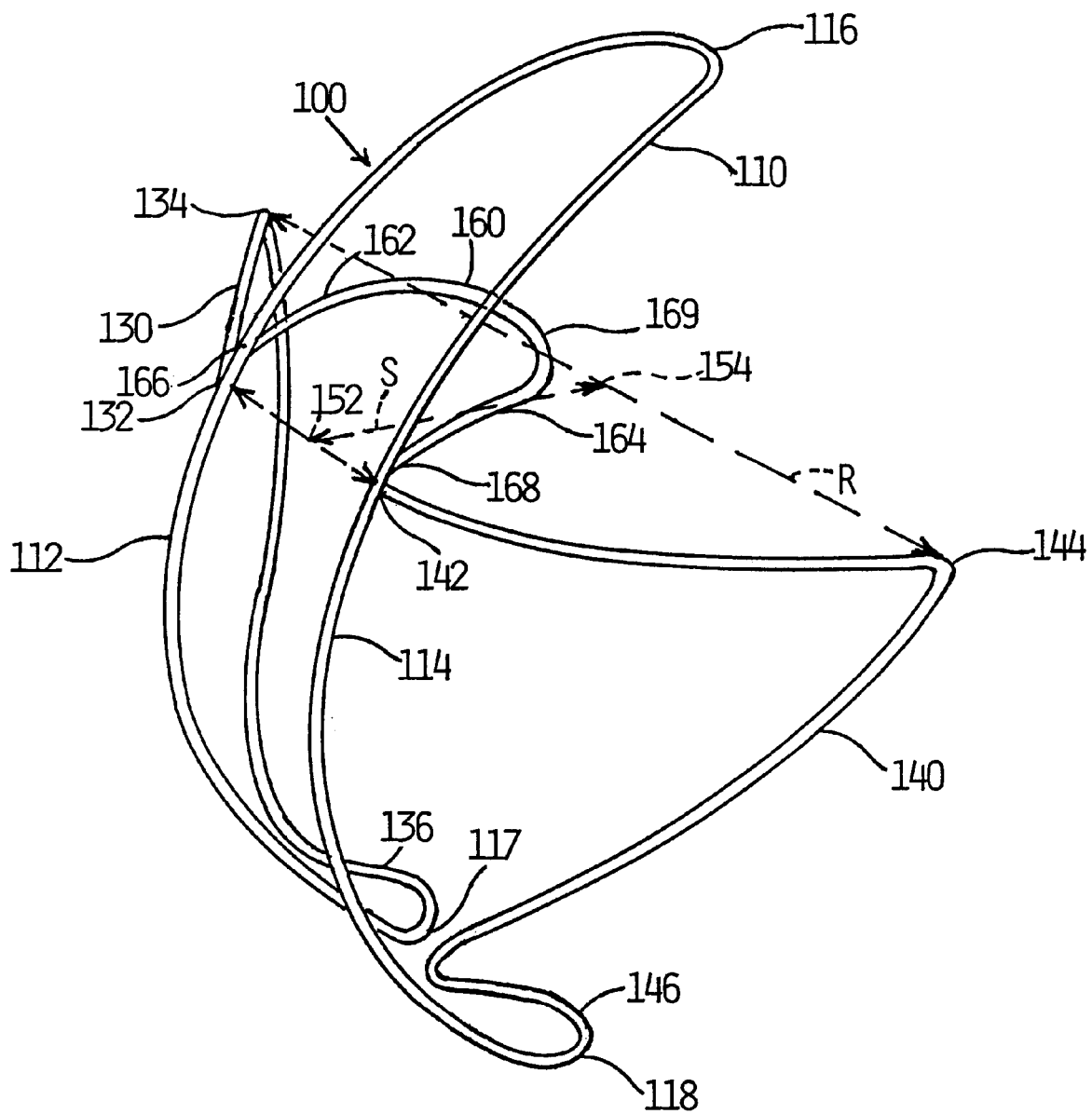
FIG. 1 is a schematic perspective view illustrating a medical tube positioning and securing device of the present invention.
Figure 2:
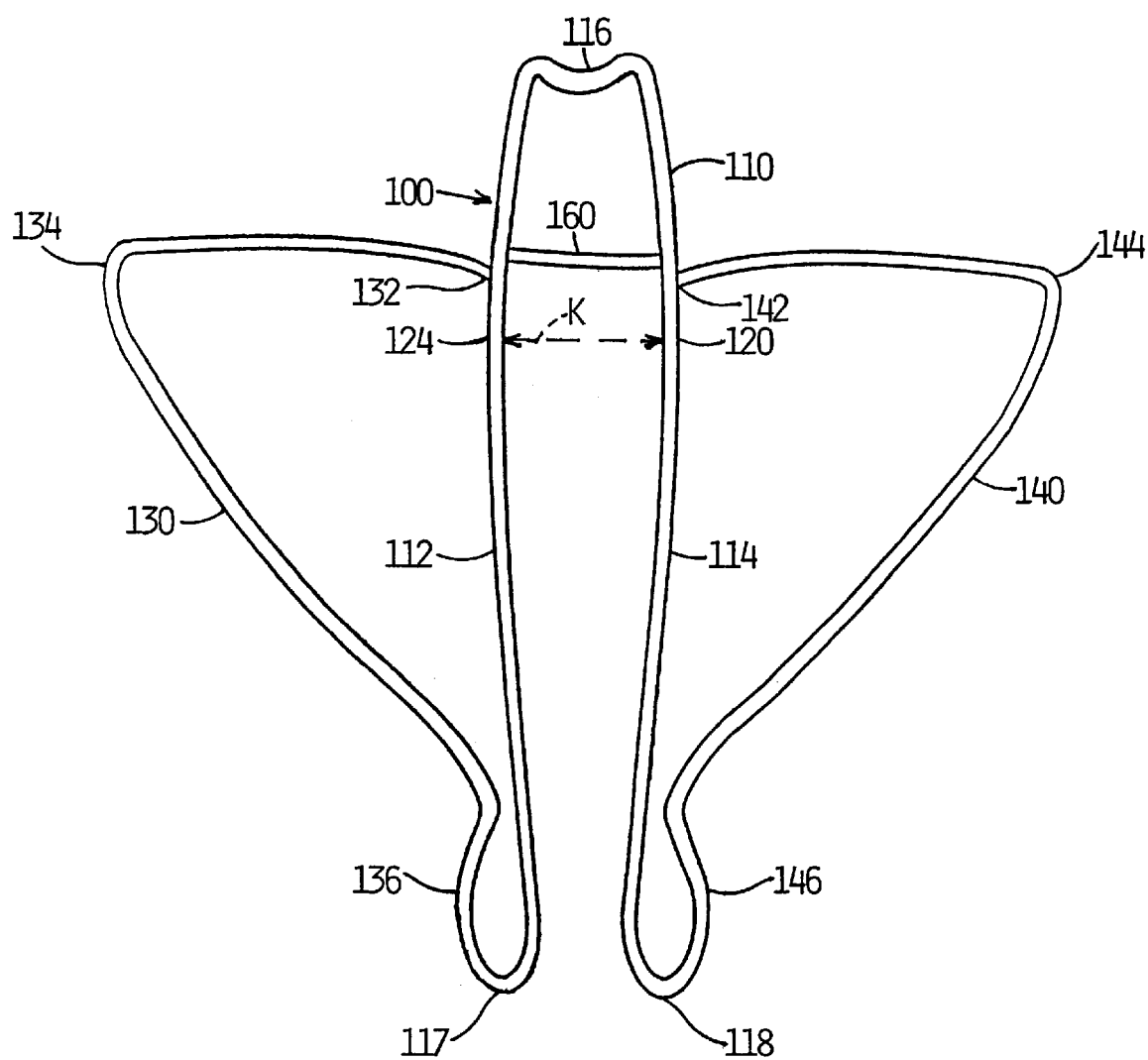
FIG. 2 is front elevation view of the device illustrated in FIG. 1.
Figure 3:
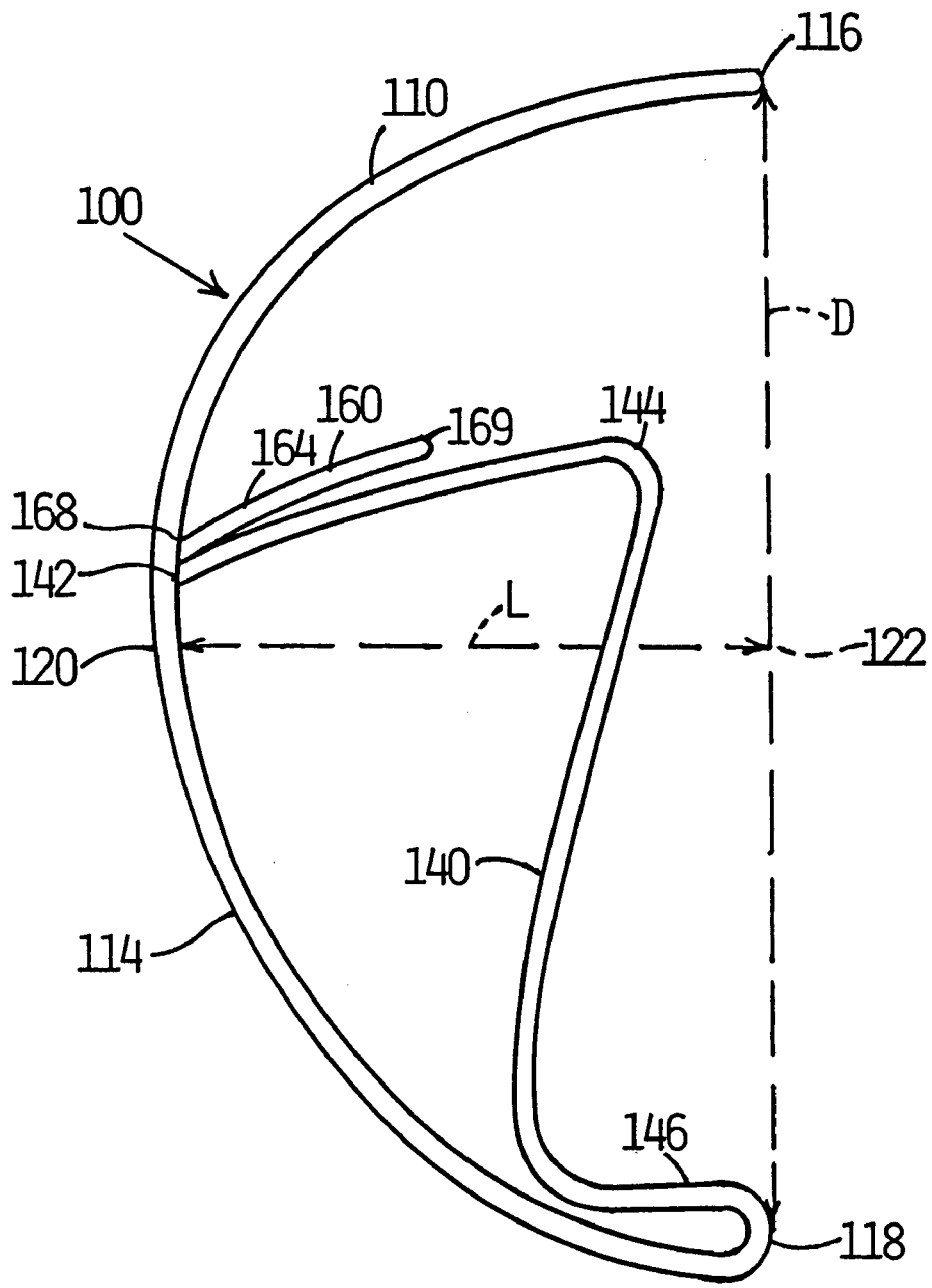
FIG. 3 is a side elevation view of the device illustrated in FIG. 1.

One embodiment of the present invention is illustrated in FIGS. 1–3, showing medical tube positioning and securing device 100 which includes a frame having several frame portions. Device 100 has an inverted U-shaped frame portion 110 which includes a first leg 112, a second leg 114 and a connecting position 116 which connects first leg 112 to second leg 114. End 117 of first leg 112 and end 118 of second leg 114 are each disposed opposite the connecting position 116. Position 116 is substantially equidistant to positions 117 and 118.

Legs 112 and 114 of device 100 are positioned in a curved plane having a predetermined degree of curvature. The degree of curvature of the plane of the legs is determined as follows. First, measure the distance D (see FIG. 3) between connecting position 116 and end 118 (or end 117). Second, determine the approximate midpoint 120 (FIG. 3) of leg 114. This midpoint is preferably within 1 cm of the exact midpoint of leg 114, more preferably within 0.3 cm of the exact midpoint. Third, measure the distance L between the approximate midpoint 120 of leg 114 and position 122 which is approximately equidistant to connecting position 116 and to end 118. Position 122 is preferably within 0.5 cm of being exactly equidistant between position 116 and end 118. The degree of curvature of the plane of legs 112 and 114 is expressed as a ratio which is distance D divided by distance L. This ratio typically ranges from about 1.1 to about 3.8. A more preferable curvature ranges from about 1.5 to about 2.1. A still more preferable degree of curvature of the curved plane of legs 112 and 114 ranges from about 1.7 to about 1.8. Distance D typically ranges from about 5 cm to about 11 cm, depending on whether the device is intended for use with a very young child or an adult.

Distance K (FIG. 2) between position 120 of leg 114 and approximate midpoint 124 of leg 112, typically ranges from about 0.5 cm to about 3 cm. Preferably, distance K ranges from about 1.5 cm to about 2.5 cm. The midpoint 124 is preferably within 1 cm of the exact midpoint of leg 114 and more preferably within 0.3 cm of the exact midpoint.

As shown in FIGS. 1–3, a first cheek frame portion 130 extends from position 132 on first leg 112, to corner position 134 on cheek portion 130 and to end 117 of first leg 112. A loop section 136 is formed in first cheek portion 130 adjacent end 117. Similarly, a second cheek frame portion 140 extends from position 142 on second leg 114, to corner position 144 and to end 118 of second leg 114. The second cheek portion has a loop section 146 adjacent end 118. Cheek portion 130 extends from first leg 112 and is disposed opposite second leg 114. Similarly, cheek portion 140 extends from second leg 114 and is disposed opposite first leg 112. Corner positions 134 and 144 and loop sections 136 and 146 form the attachment points for attaching a fastener as described more fully in connection with FIG. 12. Corner positions 134 and 144 form the extremity positions of device 100 while loop sections 136 and 146 form frame positions.

Preferably, cheek portions 130 and 140 (FIGS. 1–3) are curved inward, i.e. in the direction of an imaginary line connecting position 116 with position 118, such as a line coinciding with distance measurement D shown in FIG. 3. The degree of curvature of cheek portions 130 and 140 is determined as follows. First, determine the distance R (FIG. 1) between corner positions 134 and 144. Second, determine a position 152 which is approximately equidistant from positions 132 and 142 on legs 112 and 114 respectively. Position 152 is preferably within 0.2 cm of being equidistant from positions 132 and 142. Third, determine the distance S between position 152 and a position 154 (see FIG. 1) which is approximately equidistant from corner positions 134 and 144. The degree of curvature of the cheek portions is expressed as a ratio which is distance R divided by distance S. This ratio typically ranges from about 1.9 to about 5.6. A more preferable ratio ranges from about 2.3 to about 2.7. Distance R typically ranges from about 6 cm to about 12 cm, depending on whether the device is intended for use with a very young child or an adult. Position 152 is preferably within 0.5 cm of being equidistant between corner positions 134 and 144.

A lower jaw frame portion 160 of device 100 (see FIGS. 1–3) extends from inverted U-shaped portion 110 in the direction of an imaginary line connecting position 116 with position 118, such as the line coinciding with distance measurement D shown in FIG. 3. Lower jaw portion 160 includes a first frame member 162 and a second frame member 164. Member 162 is connected to first leg 112 at first leg position 166, while member 164 is connected to second leg 114 at second leg position 168. Members 162 and 164 are joined at position 169 which is approximately equidistant to positions 166 and 168. Preferably, position 166 is proximate position 124 (i.e. proximate the approximate midpoint of leg 112) while position 168 is proximate position 120 (i.e. proximate the approximate midpoint of leg 114), such that the distance between positions 166 and 124 is less than 1 cm.

Figure 4:
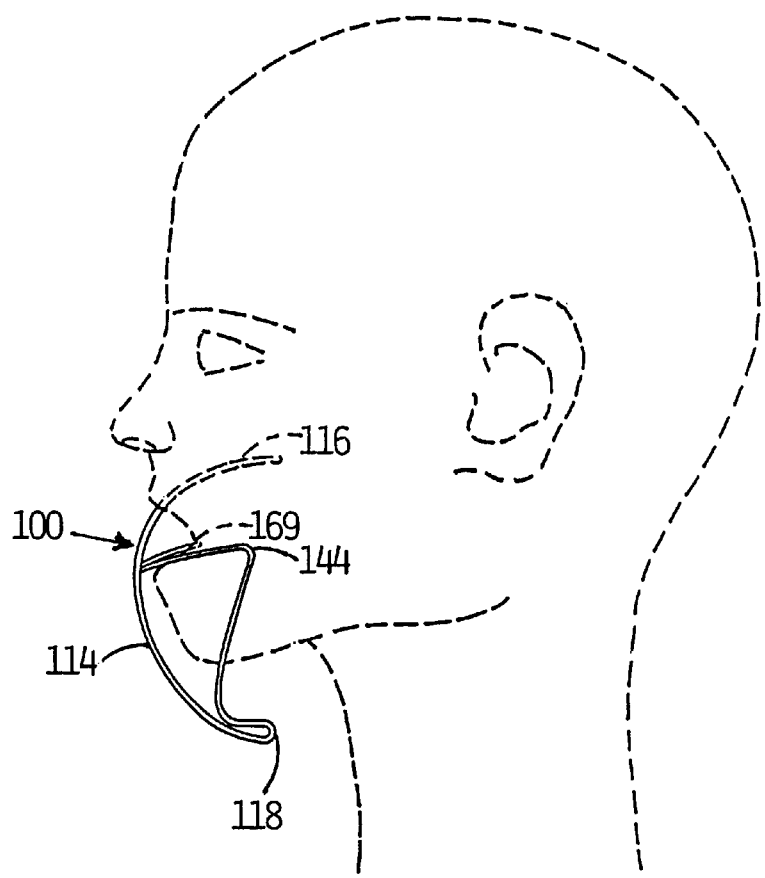
FIG. 4 is a schematic side elevation view illustrating the placement of the device shown in FIG. 3, in a patient's mouth.

An upper jaw frame portion extends along the inverted U-shaped portion between positions 166, 116 and 168. A mouth portion of device 100 is formed by the upper jaw portion and the lower jaw portion such that a patient's jaws are held open when the mouth portion is positioned inside the mouth as shown in FIG. 4. The upper jaw and mouth palate press against the upper jaw portion while the front teeth of the lower jaw press against the lower jaw portion, thereby holding the device in the mouth. Device 100 includes a central portion having the inverted U-shaped frame portion 110 which includes the upper jaw frame portion. The central portion is adapted for inserting a medical tube as will be more fully described in connection with FIG. 13.

Returning to FIGS. 1 and 3, the ratio between the length of the segment of second leg 114 between positions 168 and 116 and the length of member 164 of the lower jaw portion typically ranges from about 2.0 to about 2.8. More preferably, this ratio ranges about 2.2 to about 2.6. The length of the second leg segment between positions 168 and 116 typically ranges from about 4 cm to about 9 cm depending on whether the device is intended for use with a very young child or an adult. The distance of the gap between positions 116 and 169 ranges from about 2 cm to about 4.5 cm depending on whether the device is intended for use with a very young child or an adult. This gap distance needs to be such that it keeps the mouth open for intubation of one or more medical tubes which are inserted through inverted U-shaped portion 110 of device 100.

Curvature of the various frame portions of device 100 as described above and as shown in FIGS. 1–3, is preferable in order to (1) hold a patient's jaws open, (2) follow the contours of a patient's face without contacting the face apart from minimal contact with the lips, mouth or jaws and (3) provide attachment points for attaching a fastener for a secure and stable attachment of the device to a patient's head.

The various dimensional aspects of device 100 (FIGS. 1–3) shown in the following Table I exemplify a configuration which is suitable for many adults.

Table I

Degree of curvature of the curved plane of legs 112 and 114: about 1.7

Degree of curvature of cheek portions 130 and 140: about 2.5

Distance D: about 9.5 cm

Distance L: about 5.4 cm

Distance K: about 2.3 cm

Distance R: about 11.1 cm

Distance S: about 4.5 cm

Distance of the gap between positions 116 and 169: about 4 cm

Length of leg 114 between positions 116 and 118: about 17 cm

Figure 5:
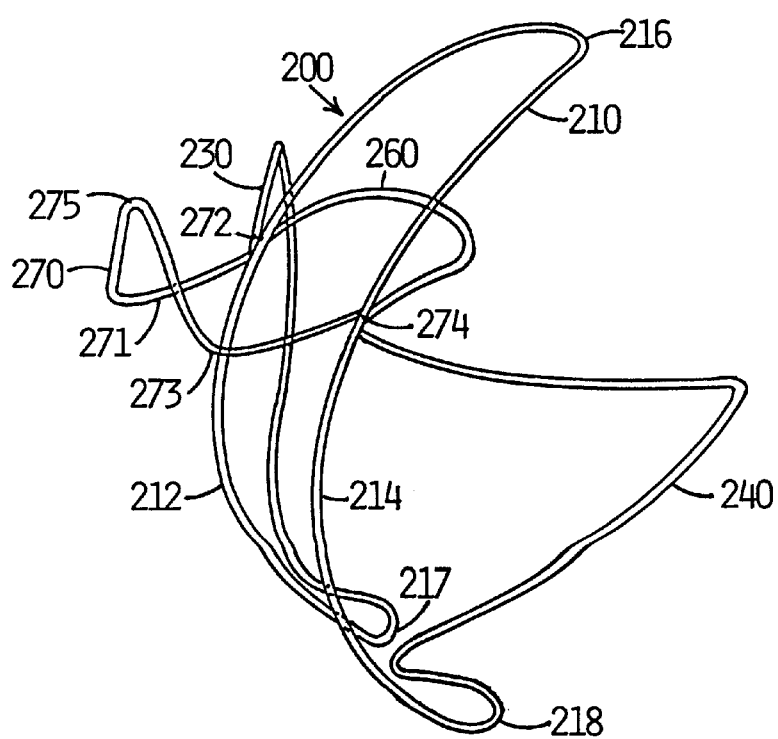
FIG. 5 is a schematic perspective view of an alternate medical tube positioning and securing device of the current invention.
Figure 6:
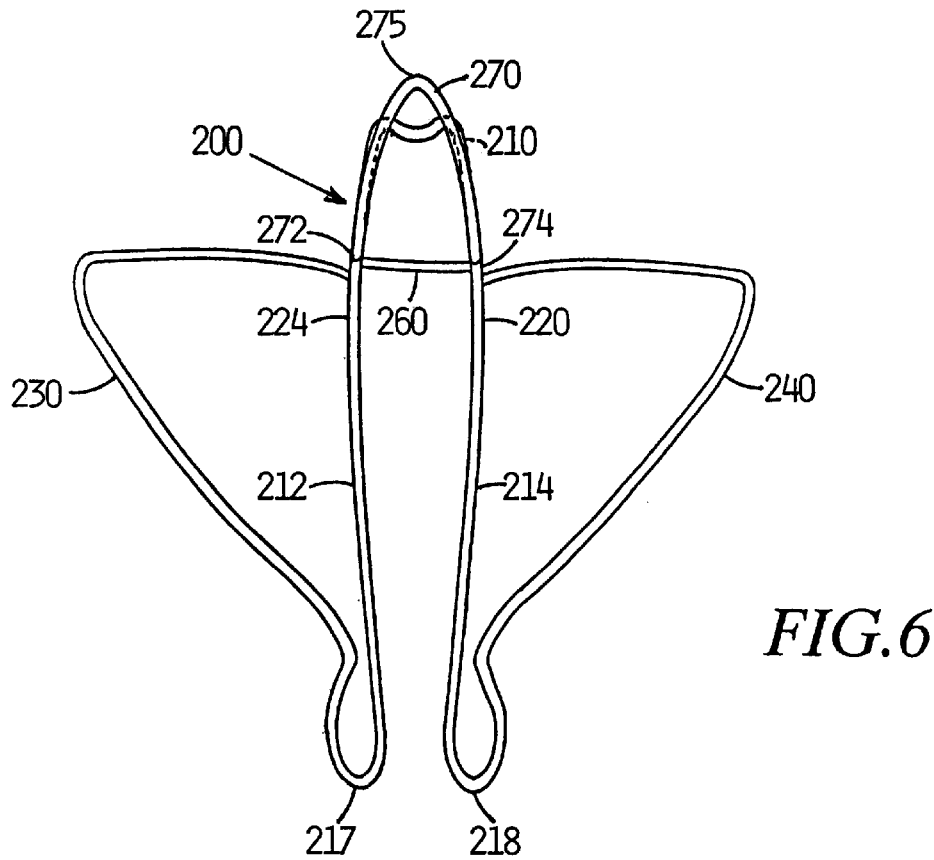
FIG. 6 is a front elevation view of the device illustrated in FIG. 5.
Figure 7:
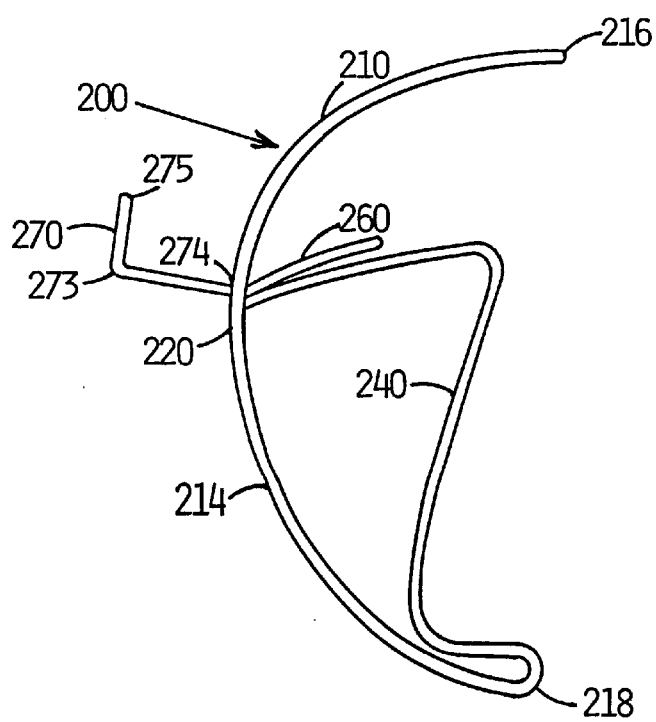
FIG. 7 is a side elevation view of the device illustrated in FIG. 5.

Another embodiment of the invention is depicted in FIGS. 5–7, showing medical tube positioning and securing device 200 having several frame portions. Device 200 is similar in shape and size as device 100, except that device 200 additionally includes a nose frame portion 270. Device 200 has an inverted U-shaped portion 210, similar to inverted U-shaped portion 110 of device 100. As shown in FIGS. 5–7 portion 210 includes a first leg 212, a second leg 214 and a connecting position 216 which connects first leg 212 to second leg 214. End 217 of first leg 212 and end 218 of second leg 214 each oppose the connecting position 216 such that position 216 is approximately equidistant to positions 217 and 218. Legs 212 and 214 have midpoints 224 and 220 respectively (see FIGS. 6 and 7). Legs 212 and 214 are positioned in a curved plane having a similar degree of curvature as legs 112 and 114 of device 100.

Figure 15:
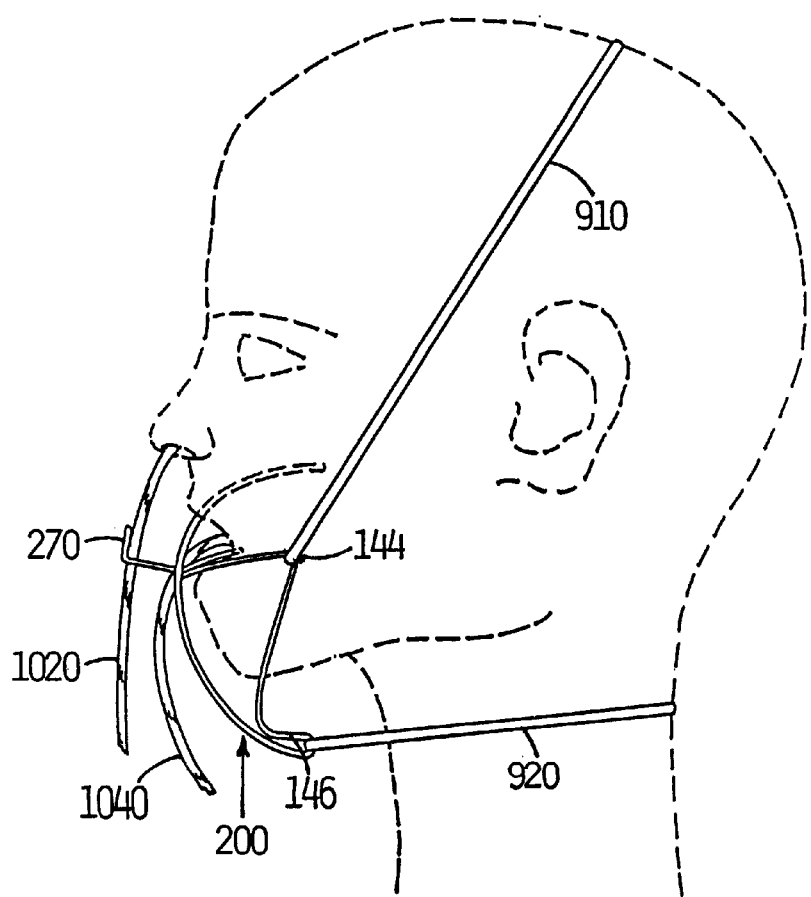
FIG. 15 is a schematic side elevation view illustrating the placement and fastening of the device shown in FIG. 7, and the insertion of medical tubes in the device and in the patient's mouth and nose.

Device 200 includes first cheek portion 230 extending from first leg 212 and second cheek portion 240 extending from second leg 214. Cheek portions 230 and 240 of device 200 are similar to cheek portions 130 and 140 respectively of device 100. The degree of curvature of cheek portions 230 and 240 is similar to the degree of curvature of cheek portions 130 and 140. Lower jaw portion 260 of device 200 is similar in shape and size as lower jaw portion 160 of device 100. The central frame portion of device 200 includes the inverted U-shaped portion 210 having an upper jaw frame portion similar to device 100. This central portion is adapted for inserting a medical tube as illustrated in FIG. 15.

Nose portion 270 of device 200 (FIGS. 5–7) includes an open loop frame member having a first loop member 271 which is attached to first leg 212 at first leg position 272 and having a second loop member 273 which is attached to second leg 214 at second leg position 274. Loop members 271 and 273 extend from legs 212 and 214 in a direction generally opposite the direction of lower jaw portion 260. Loop members 271 and 273 are joined at loop position 275, at which position loop members 271 and 273 are positioned in a direction which is substantially parallel to a plane which is tangential to the plane of curvature of legs 212 and 214 at leg midpoints 220 and 224. Nose portion 270 provides a structure for positioning and securing a medical tube which is intubated in the nose, as will be more fully explained in connection with FIG. 15.

Figure 8:
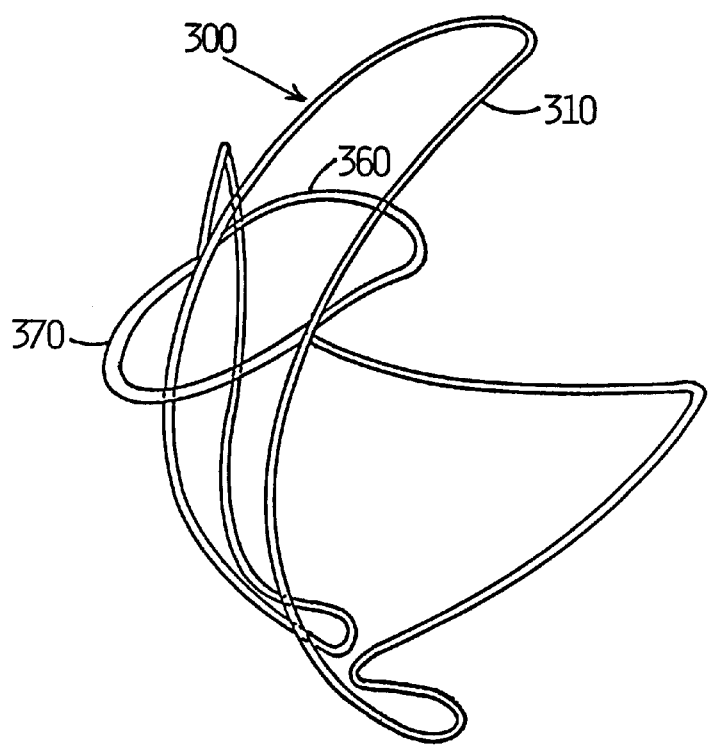
FIG. 8 is a schematic perspective view of an alternate medical tube positioning and securing device of the present invention.

Medical tube positioning and securing device 300 (FIG. 8) illustrates an alternate embodiment of device 200. Device 300 is similar in shape and size as device 200, except that nose portion 370 of device 300 is different from nose portion 270 of device 200. As shown in FIG. 8, nose portion 370 includes an open loop frame member which extends from inverted U-shaped portion 310 in a direction generally opposite the direction of lower jaw portion 360. Unlike nose portion 270 of device 200, nose portion 370 of device 300 does not have any segments which are substantially parallel to the tangent of the plane of curvature of the legs at the leg midpoints.

Figure 9:
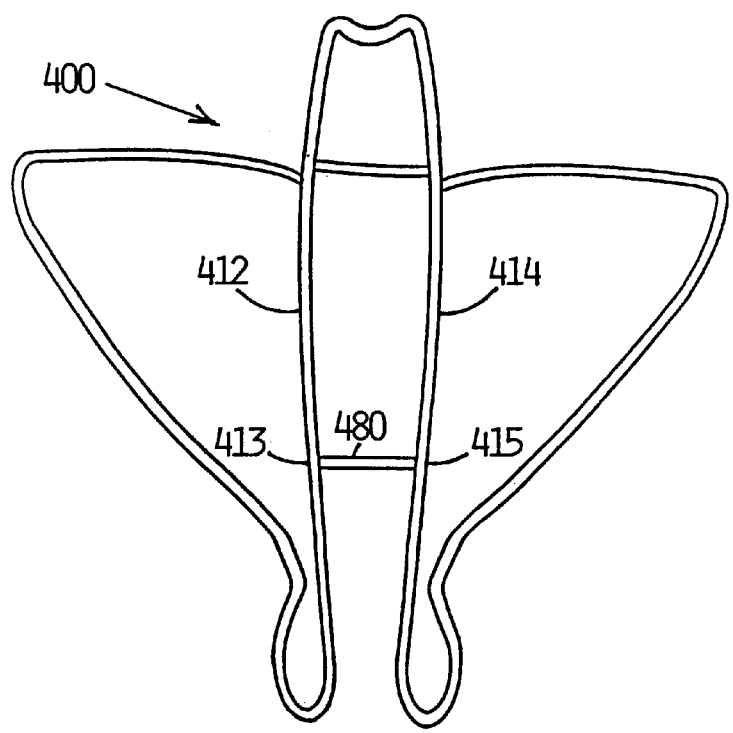
FIG. 9 is a front elevation view of an alternate medical tube positioning and securing device of the current invention.

Tube positioning and securing device 400, as shown in FIG. 9, provides an alternate embodiment of device 100. Device 400 is similar in shape and size as device 100, except that device 400 additionally includes a cross member 480 which is attached to first leg 412 and to second leg 414 at first leg position 413 and second leg position 415 respectively. Cross member 480 is preferably fabricated as a frame member, and is preferably rigidly attached to each of the two legs. Cross member 480 strengthens the device, particularly when the tube positioning and securing device is formed of thin or relatively low strength frame portions. Device 400 provides a closed loop frame portion between the upper jaw portion and cross member 480.

Figure 10:
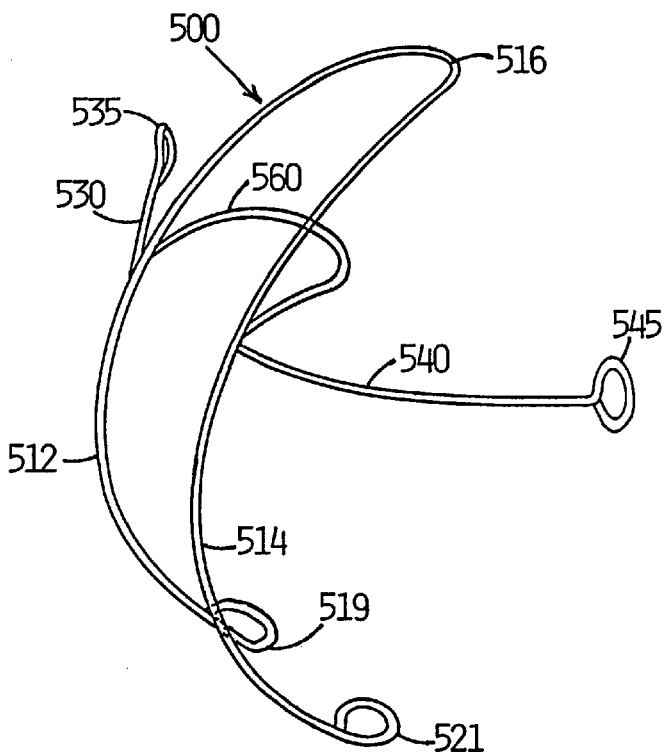
FIG. 10 is a schematic perspective view of an alternate medical tube positioning and securing device of the present invention.
Figure 11:
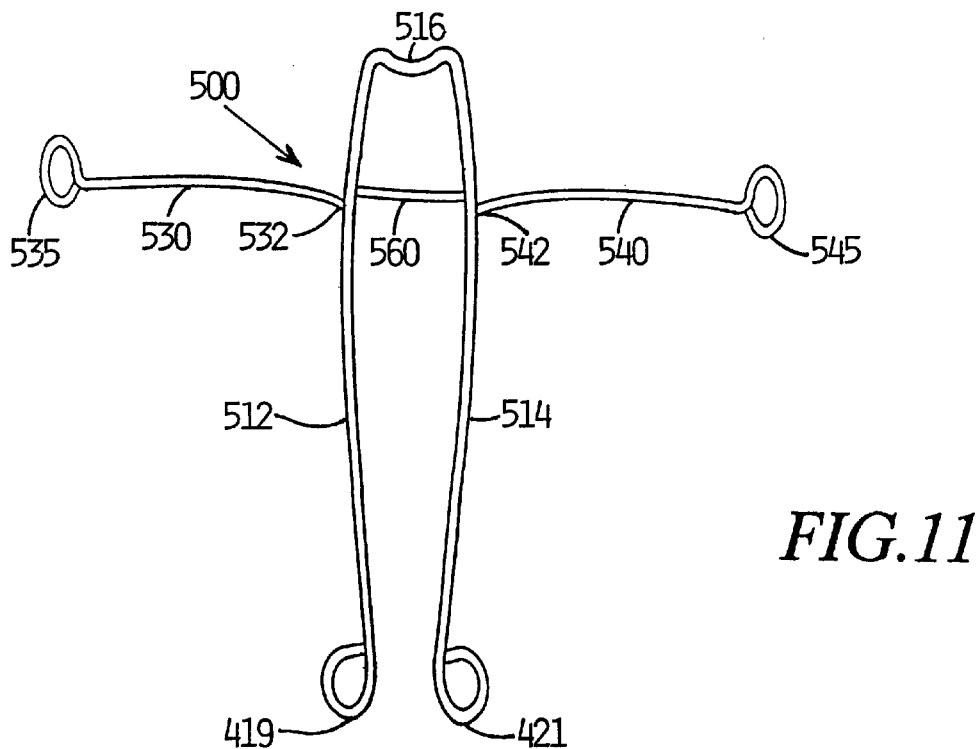
FIG. 11 is a front elevation view of the device illustrated in FIG. 10.

FIGS. 10 and 11 show tube positioning and securing device 500 which is an alternate embodiment of device 100. Device 500 differs from device 100 in the configuration of the cheek portions. Cheek portions 530 and 540 of device 500 are connected to legs 512 and 514 of inverted U-shaped portion 510 at positions 532 and 542 respectively. Cheek portions 530 and 540 have unattached ends forming loop sections 535 and 545 respectively. Legs 512 and 514 are connected at connecting position 516 and end at loop sections 519 and 521 respectively. Legs 512 and 514 are positioned in a plane having a degree of curvature which is similar to device 100. Legs 512 and 514 of device 500 have a similar length as legs 112 and 114 of device 100. The degree of curvature of cheek portions 530 and 540 of device 500 is similar to the degree of curvature of the cheek portions of device 100. Lower jaw portion 560 of device 500 has a similar size and shape as lower jaw portion 160 of device 100.

Loop sections 519, 521, 535 and 545 form the attachment points for attaching a fastener. Loop sections 535 and 545 form the extremity positions of device 500 while loop sections 519 and 521 form frame positions. The central frame portion of device 500 includes the inverted U-shaped frame portion 510 having an upper jaw frame portion similar to device 100. This central portion is adapted for inserting a medical tube.

Suitable materials of construction for the devices of the present invention include metal and plastics. It is preferable to provide a coating of soft or pliable polymer, such as rubber or plastic, on the mouth portion of the devices of the present invention, in order to reduce the patient's possible discomfort which can be caused by pressure from the mouth portion on the patient's palate or jaws. Preferably, the thickness and physical properties of the frame portions are such that the cheek and mouth portions are hand bendable, i.e. capable of being bend without using tools by a typical adult, in order to achieve an optimal fit between the device and the patient.

The devices can, for example, be fabricated using frame portions made of metal wire, such as, stainless steel wire having, for example, a diameter ranging from about 0.5 mm to about 2.5 mm, more preferably ranging from about 0.7 mm to about 1.5 mm. The particular type or grade of stainless steel is not critical for use in the devices of the present invention. The cross sectional configuration of the metal wire is not critical. This includes for example, round, oval, rectangular, square and triangular configurations. Preferable cross sectional configurations include round and oval. Methods of fabricating the devices of the present invention using metal wire include commonly known techniques for bending wire to obtain a desired configuration and commonly known techniques for joining wire portions such as welding and adhesively bonding. Another suitable metal wire for the present invention includes K-wire which can be bent relatively easily. The frame portions of the present invention can also be fabricated using plastics such as nylon, polycarbonate and acrylonitrile butadiene styrene (ABS). The preferred thickness of the frame in the plastic frame portions ranges from 1 mm to about 3 mm. The devices of the present invention can be fabricated from plastics using commonly known plastics fabricating techniques, such as, injection molding.

As previously described in connection with FIG. 4, device 100 can be held in the mouth through pressure from both jaws on the mouth portion, particularly when the patient will need the device only for a relatively short time. However, it is preferable to use a fastener in conjunction with device 100. The purpose of the fastener is to keep the device secure in place such that it is not accidentally re-positioned or moved and also to make removal of the device by the patient relatively difficult.

Figure 12:
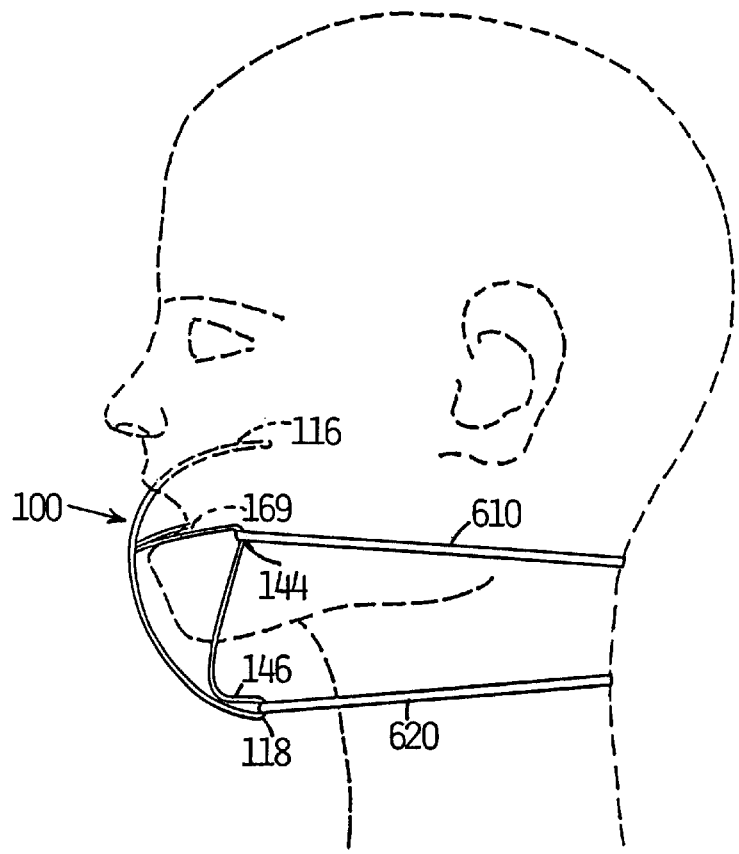
FIG. 12 is a schematic side elevation view illustrating the placement and fastening of the device shown in FIG. 1, on a patient's head.

A wide variety of fasteners has been found to be suitable for use with the devices of the present invention, such fasteners include straps and attaching means for attaching the strap to the tube securing device. For example, FIG. 12 illustrates the use of a fastener which includes straps 610 and 620 to fasten device 100. Strap 610 extends below the patient's ears and around the back of the head near the base of the skull. One end of strap 610 is attached to corner position 144 of device 100 as shown in FIG. 12, the other end is attached to corner position 134 (not shown in FIG. 12). Strap 620 extends around the back of the patient's neck and is attached to loop section 146 (FIG. 12) and to loop section 136 (not shown in FIG. 12). While it is preferable to use a fastener which attaches to four attachment points (see for example FIG. 12), the device is also operable when only two attachment points are used such as strap 610, attached to extremity positions 134 and 144.

The type of fastener strap, such as strap 610 shown in FIG. 12, which can be used in conjunction with device 100 and the other devices of the present invention is not critical. For example, pliable straps made of fabric, cloth, leather, rubber or plastic are suitable. A preferred strap includes a hypo-allergenic cotton which has a foam layer, these straps are well known to those skilled in the art. Straps which are entirely or partly elastic are also suitable for these devices. The means for attaching the strap to device 100 and to the other embodiments of the present is not critical. Suitable attaching means include conventional hook-and-loop structures, conventional male and female snap buttons, conventional clips, conventional adhesive tape or adhesive patches and lines, strings, plastic strips or cloth strips which are capable of being tied to the devices.

Figure 13:
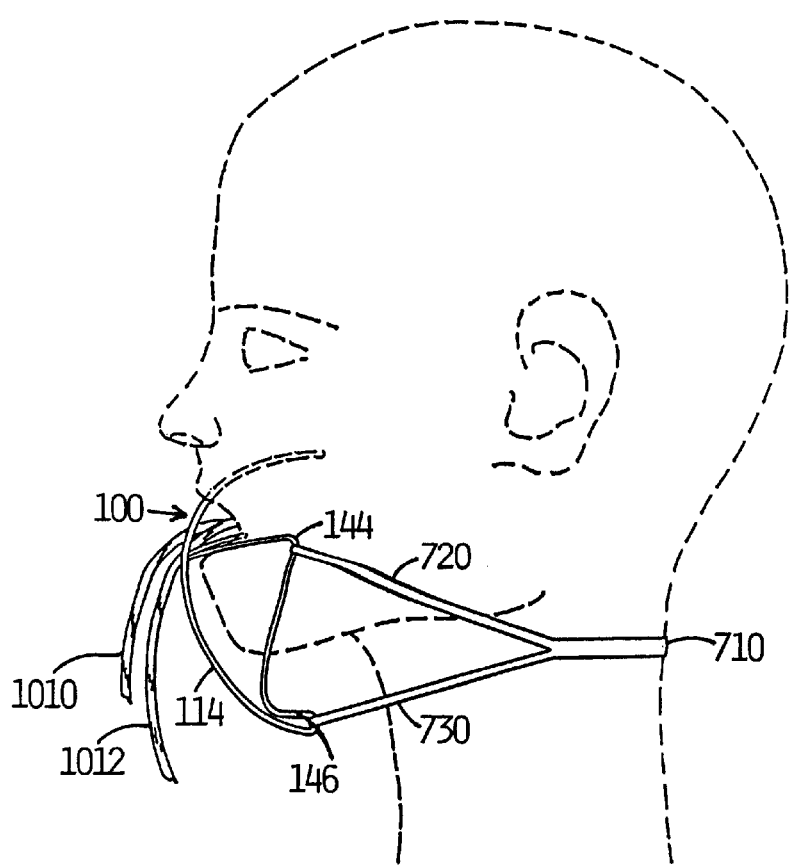
FIG. 13 is a schematic side elevation view illustrating the placement and fastening of the device shown in FIG. 1, and the insertion of medical tubes in the device and in the patient's mouth.

An alternative fastener is shown in FIG. 13, wherein device 100 is fastened by means of a strap 710 which has bifurcated ends. Bifurcated ends 720 and 730 are attached to corner position 144 and to loop section 146 respectively of device 100. Strap 710, similarly has two bifurcated ends for attachment to corner position 134 and to loop section 136 (not shown in FIG. 13). Such bifurcated straps can be fabricated by combining two single straps by means of adhesive tape, as will be described in connection with FIG. 14. Suitable attaching means for attaching bifurcated straps to the devices of the present invention include the attaching means which have been described above in connection with straps 610 and 620.

Figure 14:
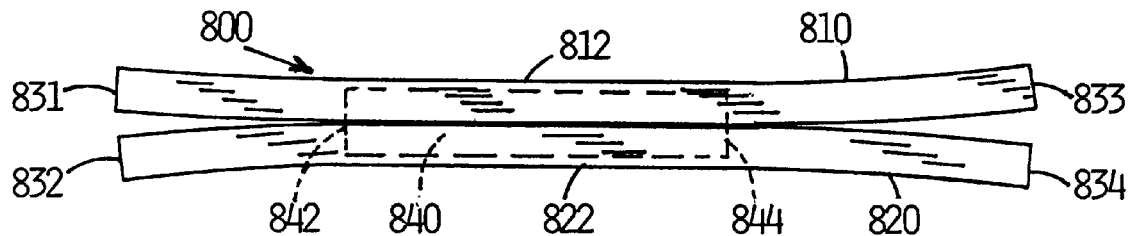
FIG. 14 is a top elevation view of a bifurcated fastening strap of the current invention.

One embodiment of the novel bifurcated straps for use with the tube positioning and securing devices of the present invention is illustrated in FIG. 14, showing bifurcated strap 800. Medial sections 812 and 822 of straps 810 and 820 respectively are adhesively attached to adhesive tape 840 by bringing these medial sections into contact with the adhesive surface of adhesive tape 840 having a first end 842 and a second end 844. Medial sections 812 and 822 are placed adjacent each other. Bifurcated strap 800 has bifurcated ends 831 and 832 extending from adhesive tape end 842, and bifurcated ends 833 and 834 extending from adhesive tape end 844. Suitable straps for forming bifurcated straps include the pliable straps described above in connection with straps 610 and 620.

An alternative fastener configuration is shown in FIG. 15 where strap 910 extends in front of the ears and around the head at its crown. Strap 910 is attached to corner position 144 of device 100 (FIG. 15) and to corner position 134 (not shown in FIG. 15). Strap 920 is positioned and attached similar to strap 620 as shown in FIG. 12.

Device 500, illustrated in FIGS. 10 and 11, is fastened in a similar manner as device 100 using loops 535, 545, 519 and 521 of device 500, instead of corner positions 134 and 144, and loop sections 136 and 146 respectively of device 100.

FIG. 13 illustrates the positioning of medical tubes 1010 and 1012 using the present invention. The tubes are inserted through the open space between legs 112 and 114 of device 100 and then intubated in the mouth after device 100 has been fastened with a suitable fastener as described above in connection with FIGS. 12–15. Once tubes 1010 and 1012 have been positioned appropriately for their respective medical functions, tubes 1010 and 1012 are secured to one or more frame portions or frame members of device 100 using suitable securing means. A frame member as defined herein includes any segment of any frame portion. Suitable securing means (not shown) include (1) adhesive tape which is wrapped around a tube and a frame member, (2) line, string, plastic or cloth strip which is tied around a tube and a frame member, (3) metal wire or metal strip which is tied around a tube and a frame member and (4) plastic tie strap which is tied around a tube and a frame member, this type of strap is commonly referred to as a "cable tie" which is typically formed in one piece having an elongated flexible strap with ratchet serrations on one side and a head at one end of the strap wherein the head has an aperture with a pawl for engaging the ratchet serrations of the strap when the free end of the strap is passed through the aperture. Examples of suitable cable ties are disclosed in U.S. Pat. No. 4,009,509 (McCormick, 1977), herein incorporated by reference. The most suitable frame portion for securing a tube which is positioned in the patient's mouth is the inverted U-shaped portion.

Positioning of medical tubes which are intubated in a patient's nose is illustrated in FIG. 15 showing the use of nose portion 270 of medical tube securing device 200. Medical tube 1020 is inserted through the open loop frame member of nose portion 270 and then intubated in the nose after the device has been fastened with a suitable fastener, using for example straps 910 and 920. Once tube 270 has been positioned appropriately, it is secured (not shown) to the nose portion. Suitable securing means include the securing means which have been described above in connection with the securing means for tubes 1010 and 1020 depicted in FIG. 13. Alternately, a medical tube similar to tube 1020 can be positioned (not shown) on the outside of nose portion 270 of device 200 and subsequently secured to the nose portion. One or more medical tubes such as tube 1040 (FIG. 15) can be intubated in the mouth and secured to device 200 in conjunction with tube 1020 which is inserted in the nose. Nose portion 370 of device 300, shown in FIG. 8, is used in a similar way as nose portion 270 of device 200.

A securely positioned medical tube system as defined herein includes devices of the present invention wherein one or more medical tubes are introduced in the device and secured to a frame portion or to a frame member of the device.

The medical tube holding or positioning and securing devices of the present invention result in significantly improved performance compared with prior art devices. For example, the frame portions combined with the fasteners of these devices result in very limited contact between the devices and the patient's nose, mouth, lips or skin thereby greatly reducing a patient's discomfort and greatly reducing the potential for nose, mouth, lip or skin irritation. The frame structure and the lack of a bite block greatly facilitate inspection of and access to a patient's mouth, potentially resulting in a more optimal medical treatment and improved mouth and nose hygiene. When a hand bendable frame material is used, the medical practitioner can manually adjust the fit of the device in the patient's mouth and adjust the degree of curvature of the cheek portions such that the cheek portions are positioned substantially parallel to the patient's face, without touching the patient's face.

The configuration of the devices of the current invention together with the use of suitable fasteners result in securely fastening the medical tubes in the appropriate position in a patient's nose or mouth. The fasteners are preferably attached to four positions, loops or loop sections on each device resulting in a four point attachment system in addition to contact between the device and the patient's upper and lower jaws. However, even though the tubes are thus securely fastened in a patient's mouth, it has been found possible to make desirable small changes in the position of the mouth portion relative to a patient's mouth, for example by moving the device laterally over a distance of a few mm without substantially changing the position of the tube in the patient's nose or throat. Frequent, small lateral re-positioning of the device further reduces the potential for patient discomfort because the points of contact between the device and the patient can be changed frequently.

The inverted U-shaped configuration of the central frame portion of the present invention provides unexpected benefits due to increased flexibility of the device when there is no rigid connection between the ends of the legs. The increased flexibility can be used to provide a slight spring bias to the fastener which is connected to the loop sections at the ends of the legs by attaching and tightening the fastener while flexing the legs towards the fastener. Also, the increased flexibility of the device enables the device to moderately absorb physical shocks, due for example, a sudden head movement.

It is important to note that the devices and fasteners of the present invention can be used without a medical practitioner having to use adhesive tape or adhesive patches. Adhesive materials tend to stick to the practitioner's gloves thereby causing tears or holes in the glove which can result in the practitioner's exposure to potentially harmful patient body fluids, compounds or microorganisms. This is particularly important during medical emergency procedures where a medical practitioner's effectiveness can be seriously hindered by the need to avoid contact with adhesive surfaces.

The invention has been described in terms of the preferred embodiment. One skilled in the art will recognize that it would be possible to construct the elements of the present invention from a variety of means and to modify the placement of components in a variety of ways. While the preferred embodiments have been described in detail and shown in the accompanying drawings, it will be evident that various further modifications are possible without departing from the scope of the invention as set forth in the following claims.

I claim:

1. A medical tube positioning and securing device comprising:
   a) a central frame portion, wherein the central frame portion has an upper jaw frame portion which is configured for contacting a patient's upper jaw and mouth palate and wherein the central frame portion is adapted for inserting a medical tube therethrough;
   b) a lower jaw frame portion extending from the central portion;
   c) a first cheek frame portion extending from the central portion;
   d) a second cheek frame portion extending from the central portion; and
   e) a mouth portion comprising the upper jaw portion and the lower jaw portion, wherein the mouth portion is adapted for placement in a patient's mouth such that the mouth remains open.

2. The device according to claim 1 additionally comprising:
   a) a first attachment point located at the first cheek frame portion;
   b) a second attachment point located at the second cheek frame portion; and
   c) a fastener for fastening the device to a patient's head, wherein the fastener is attached to the first and second attachment points.

3. The device according to claim 2 wherein the first attachment point comprises a first extremity position on the first cheek frame portion and wherein the second attachment point comprises a second extremity position on the second cheek frame portion.

4. The device according to claim 1 wherein the upper jaw frame portion is inverted U-shaped.

5. The device according to claim 1 wherein the cheek and mouth portions are hand bendable.

6. A securely positioned medical tube system comprising:
   a) a central frame portion, wherein the central frame portion has an upper jaw frame portion which is configured for contacting a patient's upper jaw and mouth palate and wherein the central frame portion is adapted for inserting a medical tube therethrough;
   b) a lower jaw frame portion extending from the central portion;
   c) a first cheek frame portion extending from the central portion; and
   d) a second cheek frame portion extending from the central portion.

7. The system according to claim 6 additionally comprising a fastener for fastening the system to a patient's head.

8. The device according to claim 6 wherein the upper jaw frame portion is inverted U-shaped.

9. The device according to claim 6 wherein the cheek and mouth portions are hand bendable.

10. A medical tube positioning and securing device comprising:

a) an inverted U-shaped frame portion including (1) a first leg having a first leg end, (2) a second leg having a second leg end, (3) a connecting position at which the first leg is connected to the second leg and wherein the connecting position is disposed opposite the first leg end and the second leg end; and (4) an upper jaw frame portion extending from the connecting position along the first leg and along the second leg, wherein the upper jaw frame portion is configured for contacting a patient's upper jaw and mouth palate;

b) a first cheek frame portion extending from the first leg and disposed opposite the second leg, wherein the first cheek portion has a first extremity position;

c) a second cheek frame portion extending from the second leg and disposed opposite the first leg, wherein the second cheek portion has a second extremity position;

d) a lower jaw frame portion extending from the first leg and from the second leg; and e) a mouth portion comprising the upper jaw portion and the lower jaw portion.

11. The device of claim 10 wherein the inverted U-shaped portion is adapted for inserting a medical tube therethrough.

12. The device according to 10 wherein the first leg and the second leg are positioned in a curved plane having a predetermined degree of curvature.

13. The device according to claim 12 wherein the predetermined degree of curvature of the plane of the first leg and the second leg ranges from about 1.1 to about 3.8.

14. The device according to claim 10 wherein the first cheek portion and the second cheek portion are curved inward and wherein the first cheek portion and the second cheek portion have a predetermined degree of curvature.

15. The device according to claim 14 wherein the degree of curvature of the first and second cheek portions ranges from about 1.9 to about 5.6.

16. The device according to claim 10 wherein the mouth portion is adapted for placement between a patient's upper jaw and a patient's lower jaw such that (1) the upper jaw and the lower jaw are held in an open position, (2) the upper jaw portion presses against the upper jaw and against the mouth palate and (3) the lower jaw portion presses against teeth of the lower jaw.

17. The device according to claim 10 additionally comprising a nose frame portion wherein the nose portion extends from the inverted U-shaped portion and wherein the nose portion is disposed opposite the lower jaw portion.

18. The device according to claim 10 additionally comprising a cross member which is attached to the first leg and to the second leg.

19. The device according to claim 10 additionally comprising a fastener for fastening the device to a patient's head wherein the fastener is attached to the first and second extremity positions.

20. The device according to claim 19 wherein the first fastener is adapted for extending around a back portion of a patient's head.

21. The device according to claim 10 additionally comprising a fastener which is attached to (1) the first extremity position, (2) the second extremity position, (3) a first frame position proximate the first leg end and (4) a second frame position proximate the second leg end.

22. The device according to claim 21 wherein the fastener comprises a first strap and a second strap.

23. The device according to claim 21 wherein the fastener comprises a bifurcated fastener including: (1) a first strap, (2) a second strap and (3) an adhesive tape having an adhesive surface which is bonded to a first medial section of the first strap and to a second medial section of the second strap.

24. The device according to claim 10 wherein the device is fabricated using metal wire.

25. The device according to claim 10 wherein the first leg and the second leg are flexibly disposed to each other.

26. The device according to claim 10 wherein the upper jaw frame portion is inverted U-shaped.

27. A method of securely positioning a medical tube in a patient's respiratory passageway comprising the steps of:

a) providing the medical tube;

b) providing a medical tube positioning and securing device comprising (1) an inverted U-shaped frame portion having an upper jaw frame portion which is configured for contacting a patient's upper jaw and mouth palate and wherein the inverted U-shaped portion is adapted for inserting the medical tube therethrough, (2) a lower jaw frame portion extending from the inverted U-shaped portion, (3) a first cheek frame portion extending from the inverted U-shaped portion, (4) a second cheek frame portion extending from the inverted U-shaped portion, wherein the second cheek frame portion is disposed opposite the first cheek frame portion and (5) a mouth frame portion including the upper jaw portion and the lower jaw portion;

c) placing the mouth portion of the medical tube positioning and securing device in the patient's mouth;

d) providing a fastener for fastening the device to a patient's head;

e) extending the fastener around a back portion of the patient's head;

f) providing attaching means for attaching the fastener to the medical tube positioning and securing device;

g) attaching the fastener to the medical tube positioning and securing device using the attaching means;

h) inserting the medical tube through the inverted U-shaped portion into the patient's respiratory passageway;

i) positioning the medical tube in the respiratory passageway such that the position is appropriate for its intended medical purpose;

j) providing a securing means for securing the medical tube to a frame portion of the device; and k) securing the medical tube to a frame portion using the securing means.

28. The method of claim 27 additionally comprising:

a) providing a first extremity position to the first cheek portion; and b) providing a second extremity position to the second cheek portion.

29. The method of claim 28 wherein the step of attaching the fastener to the device comprises the step of attaching the fastener to the first extremity position and to the second extremity position.

30. The method of claim 27 wherein the step of placing the mouth portion in the patient's mouth comprises:

a) positioning the upper jaw frame portion in contact with the upper jaw and the mouth palate; and b) positioning the lower jaw frame portion in contact with the teeth of the lower jaw.

31. The method of claim 27 wherein the step of providing a medical tube positioning and securing device additionally comprises the upper jaw frame portion having an inverted U-shaped configuration.

32. The method of claim 27 wherein the step of providing a tube positioning and securing device additionally comprises cheek and mouth frame portions which are hand bendable.

33. The method of claim 32 wherein the step of placing the mouth portion in the patient's mouth is preceded by the step of bending the cheek and mouth frame portions such that there is an optimal fit between the device and the patient.

34. A medical tube positioning and securing device comprising:
   a) a central frame portion, wherein the central frame portion has an inverted U-shaped upper jaw frame portion and wherein the central frame portion is adapted for inserting a medical tube therethrough;
   b) a lower jaw frame portion extending from the central portion;
   c) a first cheek frame portion extending from the central portion;
   d) a second cheek frame portion extending from the central portion; and
   e) a mouth portion comprising the upper jaw portion and the lower jaw portion, wherein the mouth portion is adapted for placement in a patient's mouth such that the mouth remains open.

35. A method of securely positioning a medical tube in a patient's respiratory passageway comprising the steps of:
   a) providing the medical tube;
   b) providing a medical tube positioning and securing device comprising (1) an inverted U-shaped central frame portion having an inverted U-shaped upper jaw frame portion and wherein the inverted U-shaped central frame portion is adapted for inserting the medical tube therethrough, (2) a lower jaw frame portion extending from the inverted U-shaped portion, (3) a first cheek frame portion extending from the inverted U-shaped portion, (4) a second cheek frame portion extending from the inverted U-shaped portion, wherein the second cheek frame portion is disposed opposite the first cheek frame portion and (5) a mouth frame portion including the upper jaw portion and the lower jaw portion;
   c) placing the mouth portion of the medical tube positioning and securing device in a patient's mouth;
   d) providing a fastener for fastening the device to a patient's head;
   e) using the fastener for fastening the device to the patient's head;
   f) inserting the medical tube through the inverted U-shaped portion into the patient's respiratory passageway;
   g) positioning the medical tube in the respiratory passageway such that the position is appropriate for its intended medical purpose;
   h) providing a securing means for securing the medical tube to a frame portion of the device; and
   i) securing the medical tube to a frame portion using the securing means.

* * * * *